United States Patent [19]

Mock et al.

[11] Patent Number: 5,633,364

[45] Date of Patent: May 27, 1997

[54] N[4]-SUBSTITUTED 2'-DEOXYCYTIDINE COMPOUNDS, OLIGONUCLEOTIDES INCLUDING N[4]-LABELED 2'-DEOXYCYTIDINES, AND A PROCESS FOR MAKING OLIGONUCLEOTIDES WITH N-MODIFIED 2'-DEOXYCYTIDINES

[75] Inventors: Graham A. Mock, Northborough; Douglas H. Lovern, Milford, both of Mass.

[73] Assignee: Amoco Corporation, Chicago, Ill.

[21] Appl. No.: 946,804

[22] Filed: Sep. 17, 1992

Related U.S. Application Data

[63] Continuation of Ser. No. 529,953, Jul. 23, 1990, abandoned, which is a continuation of Ser. No. 108,843, Oct. 9, 1987, Pat. No. 5,405,950, which is a continuation of Ser. No. 734,323, May 15, 1985, abandoned.

[51] Int. Cl.[6] .................... C07H 21/04; C07H 21/00; C07H 19/06
[52] U.S. Cl. .................. 536/24.3; 536/25.32; 536/28.51
[58] Field of Search .......................... 536/24.3, 25.32, 536/28.51

[56] References Cited

U.S. PATENT DOCUMENTS

| | | | |
|---|---|---|---|
| 4,097,665 | 6/1978 | Ishida et al. | 536/28.5 |
| 4,310,662 | 1/1982 | Crea et al. | 536/25.33 |
| 4,668,777 | 5/1987 | Caruthers et al. | 536/25.34 |
| 4,725,677 | 2/1988 | Köster et al. | 536/28.34 |
| 4,828,979 | 5/1989 | Klevan et al. | 536/25.33 |
| 5,091,519 | 2/1992 | Cruickshank | 536/25.33 |
| 5,405,950 | 4/1995 | Mock et al. | 536/25.32 |

OTHER PUBLICATIONS

Schulman et al., "Attachment of Protein Affinity–labeling Reagents of Variable Length and Amino Acid Specificity to E. coli tRNA[fMet]," Nucleic Acids Res., 9(5), 1203–1217 (1981).

*Primary Examiner*—John Kight
*Assistant Examiner*—L. Eric Crane
*Attorney, Agent, or Firm*—Norval B. Galloway

[57] ABSTRACT

An oligonucleotide containing at least one cytidine analog labeled at C4 with a reporter group.

23 Claims, 5 Drawing Sheets

N⁴-SUBSTITUTED 2'-DEOXYCYTIDINE COMPOUNDS, OLIGONUCLEOTIDES INCLUDING N⁴-LABELED 2'-DEOXYCYTIDINES, AND A PROCESS FOR MAKING OLIGONUCLEOTIDES WITH N-MODIFIED 2'-DEOXYCYTIDINES

This is a continuation of U.S. patent application Ser. No. 07/529,953 filed Jul. 23, 1990, now abandoned which is a continuation of U.S. patent application Ser. No. 07/108,843 filed Oct. 9, 1987, now U.S. Pat. No. 5,405,950, which is a continuation of U.S. patent application Ser. No. 06/734,323 filed May 15, 1985, now abandoned.

BACKGROUND OF THE INVENTION

This invention relates to nucleotide analogs capable of being attached to oligonucleotides and labeled for use as nucleic acid hybridization probes.

Such probes are used to detect DNA and, in some instances, RNA, characteristic of particular cells or microorganisms. Both isotopic and non-isotopic labeling methods have been used.

SUMMARY OF THE INVENTION

In general, the invention features a cytidine analog in which the cytosine base portion thereof has the formula

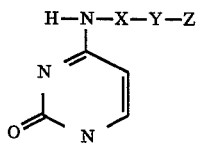

wherein Y is derived from a group capable of reacting with the N-hydroxy-succinimide ester of biotin amino caproic acid, Z is a protecting group capable of preventing Y from reacting with a phosphite, and X is a linking group connecting Y and N.

Preferably, Y is NH, Z is

and X is $(CH_2)_3$.

As will be explained in more detail below, the cytidine analogs of the invention are attached to synthetic oligonucleotide probes, and the protective group Z removed to expose the reactive group Y, which is spaced from the cytidine analog by spacer X, to prevent steric hindrance. A reporter group is then attached to reactive group Y (which may change slightly in structure in the process of deprotection; e.g., NH becomes $NH_2$), thus labeling the probe.

The invention provides rapid, simple labeling which can be precisely controlled in degree and position of label.

Other features and advantages of the invention will be apparent from the following description of the preferred embodiments thereof, and from the claims.

DESCRIPTION OF THE PREFERRED EMBODIMENTS

The drawings will first be described.

Figure 1:
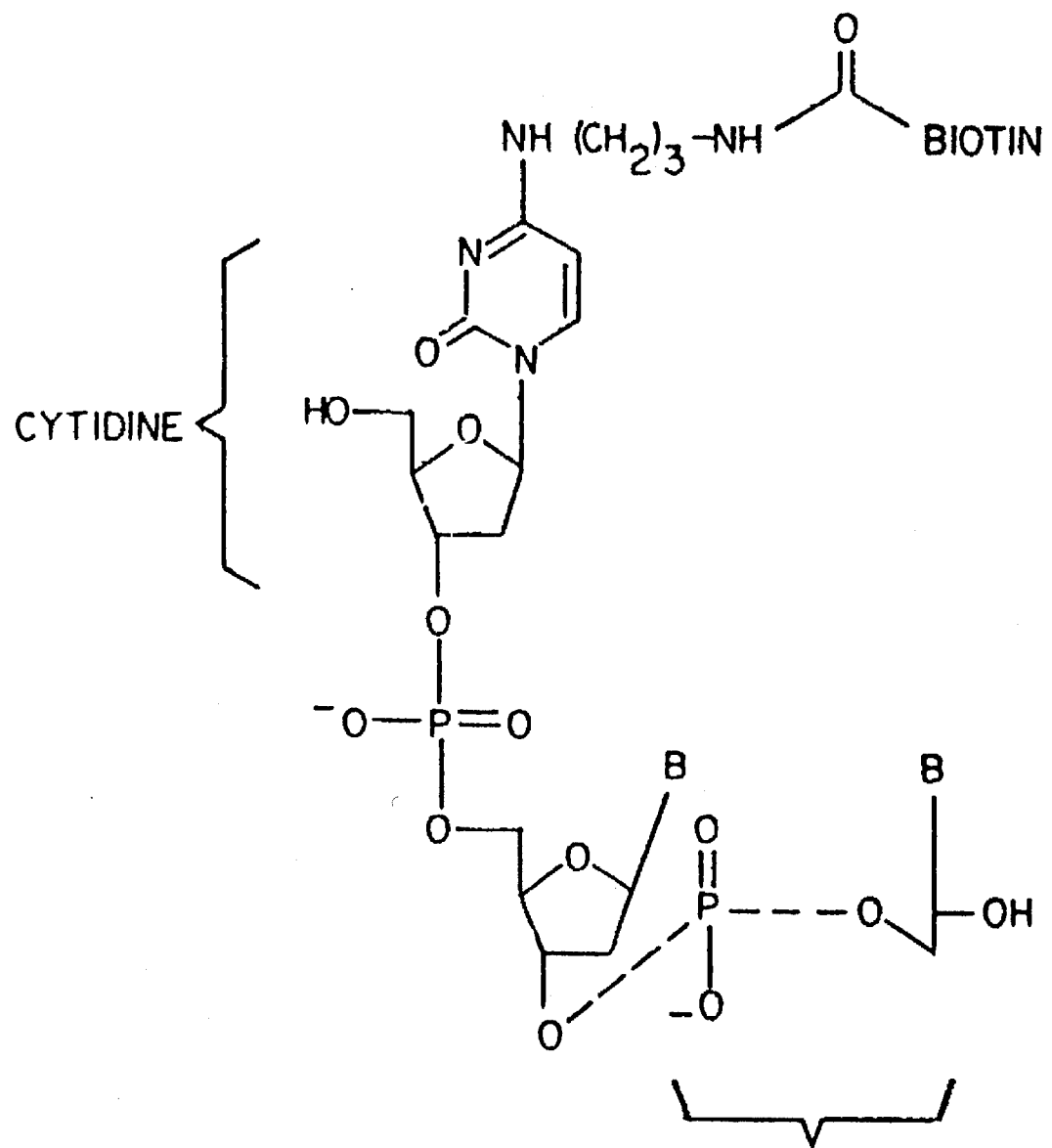

Drawings FIG. 1 is the structure of a preferred labeled oligonucleotide of the invention.

FIGS. 2-5 are the structures of the intermediates in the synthesis of said labeled oligonucleotide.

Structure

The labeled oligonucleotides of the invention have the structure given in the Summary of the Invention, above. The substituents are now described in more detail.

Reactive Group Y

Reactive group Y is derived from a group capable of reacting with the N-hydroxy-succinimide ester of biotin amino caproic acid. This does not mean that the reporter group need be biotin or a derivative thereof, but is simply a convenient way of defining the reactivity of Y necessary for its being labeled with any desired reporter group.

The presently most preferred reactive group Y is an amino group or derivative thereof. Other suitable reactive groups are S— and C—O.

Linking Group X

Linking group X does not participate directly in the derivatization reaction but rather serves the function of preventing steric hindrance between the amino group of cytidine and reactive group Y. Consequently, it is the size of X, rather than its chemical composition, that is important. Generally, X therefore can include any of a wide range of chemical substituents, provided they are not more reactive than group Y. Examples of suitable linking groups X are

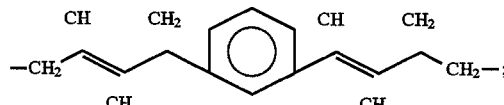

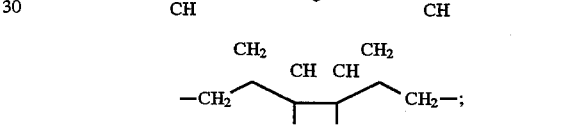

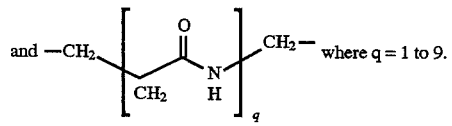

Protecting Group Z

Protecting group Z is any group which bonds to reactive group Y to prevent Y from reacting with a phosphite reagent. The protecting group Z must also be capable of being removed after the cytidine analog has been attached to the oligonucleotide, under conditions which do not substantially impair the hybridizing ability of the oligonucleotide or the reactivity of Y.

Where the reactive group Y is an amino group, suitable protecting groups are amides, e.g., N-Formyl, N-Acetyl, N-Chloroacetyl, N-Trichloroacetyl, N-Trifluoroacetyl, N-o-Nitrophenylacetyl, N-o-Nitrophenoxyacetyl, N-Acetoacetyl, N-3-Phenylpropionyl, N-3-(p-Hydroxyphenyl)propionyl, N-2-Methyl-2-(o-nitrophenoxy) propionyl, N-2-Methyl-2-(o-phenylazophenoxy)propionyl, N-4-Chlorobutyryl, N-o-Nitrocinnamoyl, N-Picolinoyl, N-(N'-Acetylmethionyl), N-Benzoyl, N-Phthaloyl, and N-Dithiasuccinoyl.

Other suitable amino protecting groups are carbamates, e.g, Methyl Carbamyl, 9-Fluorenylmethyl Carbamyl, 2,2,2-Trichloroethyl Carbamyl, 2-Trimethylsilylethyl Carbamyl, 1,1-Dimethylpropynyl Carbamyl, 1-Methyl-1-phenylethyl Carbamyl, 1-Methyl-1-(4-biphenylyl)ethyl Carbamyl, 1-1-Dimethyl-2-haloethyl Carbamyl, 1,1-Dimethyl-2-cyanoethyl Carbamyl, t-Butyl Carbamate, Cyclobutyl Carbamyl, 1-Methylcyclobutyl Carbamyl, 1-Adamantyl Carbamyl, Vinyl Carbamyl, Allyl Carbamyl, Cinnamyl Carbamyl, 8-Quinolyl Carbamyl, N-Hydroxypiperidinyl Carbmyl, 4,5-Diphenyl-3-oxazolin-2-one, Benzyl Carbamyl, p-Nitrobenzyl Carbamyl, 3,4-Dimethoxy-6-nitrobenzyl Carbamyl, 2,4-Dichlorobenzyl Carbamyl, 5-Benzisoxazolylmethyl Carbamyl, 9-Anthrylmethyl Carbamyl, Diphenylmethyl Carbamyl, Isonicotinyl Carbamyl, S-Benzyl Carbamyl, and N-(N'-Phenylaminothiocarbonyl) Derivatives.

Other suitable amino protecting groups include N-Allyl, N-Phenacyl, N-3-Acetoxypropyl, Quaternary Ammonium Salts, N-Methoxymethyl, N-Benzyloxymethyl, N-Pivaloyloxymethyl, N-Tetrahydropyranyl, N-2,4-Dinitrophenyl, N-Benzyl, N-o-Nitrobenzyl, N-Di(p-methoxyphenyl)methyl, N-Triphenylmethyl, N-(p-Methoxyphenyl)diphenylmethyl, N-Diphenyl-4-pyridylmethyl, N-2-Picolyl N'-Oxide, N,N'-Isopropylidene, N-Benzylidene, N-p-Nitrobenzylidene, N-Salicylidene, N-(5,5-Dimethyl-3-oxo-1-cyclohexenyl), N-Nitro, N-Oxide, N-Diphenylphosphinyl, N-Dimethylthiophosphinyl, N-Benzenesulfenyl, N-o-Nitrobenzenesulfenyl, N-2,4,6-Trimethylbenzenesulfonyl, N-Toluenesulfonyl, N-Benzylsulfonyl, N-Trifluoromethylsulfonyl, and N-Phenacylsulfonyl.

Where reactive group Y is a thiol group, suitable protecting groups include S-Benzyl Thioether, S-p-Methoxybenzyl Thioether, S-p-Nitrobenzyl Thioether, S-4-Picolyl Thioether, S-2-Picolyl N-Oxide Thioether, S-9-Anthrylmethyl Thioether, S-Diphenylmethyl Thioester, S-Di(p-methoxyphenyl)methyl Thioether, S-Triphenylmethyl Thioether, S-2,4-Dinitrophenyl Thioester, S-t-Butyl Thioether, S-Isobutoxymethyl Hemithioacetal, S-2-Tetrahydropyranyl Hemithioacetal, S-Acetamidomethyl Aminothioacetal, S-Cyanomethyl Thioether, S-2-Nitro-1-Phenylethyl Thioether, S-2,2-Bis(carboethoxy)ethyl Thioether, S-Benzoyl Derivative, S-(N-Ethylcarbamyl), and S-Ethyl Disulfide.

Where the reactive group Y is a carboxyl group, suitable protecting groups include Methyl Ester, Methoxymethyl Ester, Methylthiomethyl Ester, Tetrahydropyranyl Ester, Benzyloxymethyl Ester, Phenacyl Ester, N-Phthalimidomethyl Ester, 2,2,2-Trichloroethyl Ester, 2-Haloethyl Ester, 2-(p-Toluenesulfonyl)ethyl Ester, t-Butyl Ester, Cinnamyl Ester, Benzyl Ester, Triphenylmethyl Ester, Bis(o-nitrophenyl)methyl Ester, 9-Anthrylmethyl Ester, 2-(9,10-Dioxo)anthrylmethyl Ester, Piperonyl Ester, Trimethylsilyl Ester, t-Butyldimethylsilyl Ester, S-t-Butyl Ester, 2-Alkyl-1,3-oxazolines, N,N-Dimethylamide, N-7-Nitroindoylamide, Hydrazides, N-Phenylhydrazide, and N,N-Diisopropylhydrazide.

Sugar Moiety

For convenience and economy, it is preferred that the sugar moiety to which the cytosine base is bonded have the conventional 5-membered heterocyclic configuration, with oxygen and four carbon atoms constituting the ring. Strict adherence to this configuration is not important to the labeling or hybridization reactions, however, and various other substituents, e.g., S, NH, or $CH_2$, can be substituted for the ring oxygen if desired.

Similarly, the group bonded to $C_5$ of the sugar moiety is most conveniently a hydroxyl group in which the hydrogen is replaced by a protecting group which is capable of preventing the reaction of the hydroxyl with a phosphite reagent; this protecting group can be any conventional hydroxyl protecting group, e.g., 4,4'-dimethoxytrityl (DMT), ethers such as methyl ether, esters such as acetate esters, and cyclic acetals and ketals such as ethylidine.

If desired, the group attached to $C_5$ of the sugar moiety can be, rather than a protected hydroxyl group, a conventionally protected S group.

Linkage to Oligonucleotide

The cytidine analog is attached to the oligonucleotide by means of a linking group substituted for the hydrogen in the hydroxyl group bonded to $C_3$ of the sugar moiety. As mentioned above, a preferred linking group is

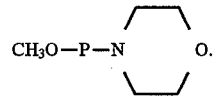

A more preferred linking group is

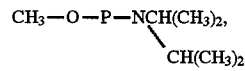

and most preferred is

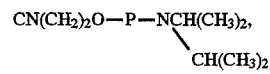

which uses a β-cyanoethyl group in place of the methyl. Any other suitable phosphorus-containing group can be used, however, e.g., other phosphite groups, or phosphate groups, including groups containing more than one phosphorus atom.

Reporter Group

Following the attachment of the cytidine analog to the oligonucleotide and the deprotection of reactive group Y, Y is reacted with any suitable reporter group. The reporter group can be directly detectable, as in the case of fluorophores such as fluorescein, or it can be a group which confers binding specificity on the oligonucleotide to enable detection by a subsequent compound or series of compounds. One well-known example of the latter is the system using biotin, avidin, and enzyme, and a substrate for the enzyme which produces a detectable change when acted on by the enzyme.

Synthesis

The synthesis of the labeled oligonucleotides of the invention is carried out generally as follows.

The first step is to synthesize a cytidine analog having the formula given in the Summary of the Invention, above. The analog has, attached to the amino group at C4, a linking group X, a reactive group, or derivative thereof, Y, and a protective group Z. To construct the analog, X and Y are attached to the amino group of C4 of cytidine, and the reactive group Y is then protected with protective group Z.

The next step is to attach the cytidine analog to the 5' end of an oligonucleotide to be used as a hybridization probe. Following this step, additional nucleotides can be attached to the cytidine analog, including additional cytidine analogs, to give as many labeled positions in the oligonucleotide as desired, at precisely predetermined positions. This is conveniently done using commercially available DNA synthesizers, into which the cytidine analog has been loaded.

Finally, the cytidine analog is deprotected and a label attached at Y to yield a labeled oligonucleotide.

Referring now to FIG. 1, there is shown a labeled oligonucleotide in which X is $(CH_2)_3$, Y is NH, and the detectable label is biotin, a well-known reporter compound whose affinity for avidin has previously rendered it useful in labeling DNA probes.

Figure 2:
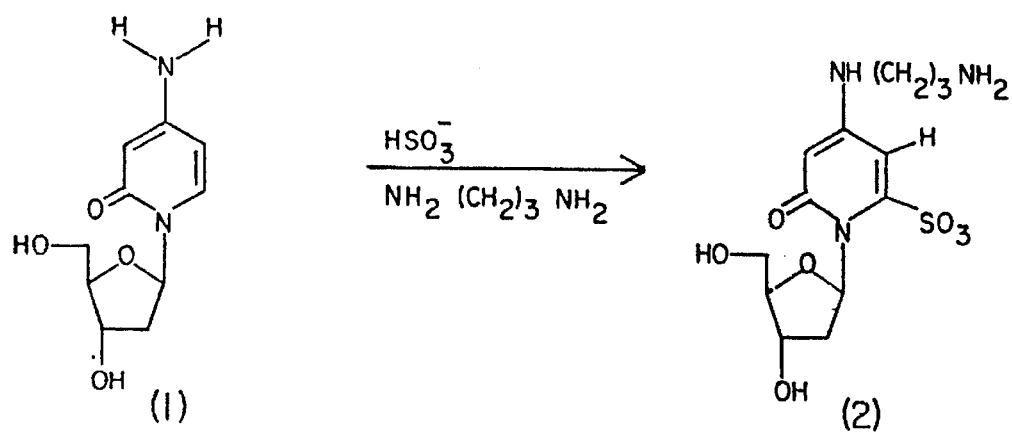
Figure 2:
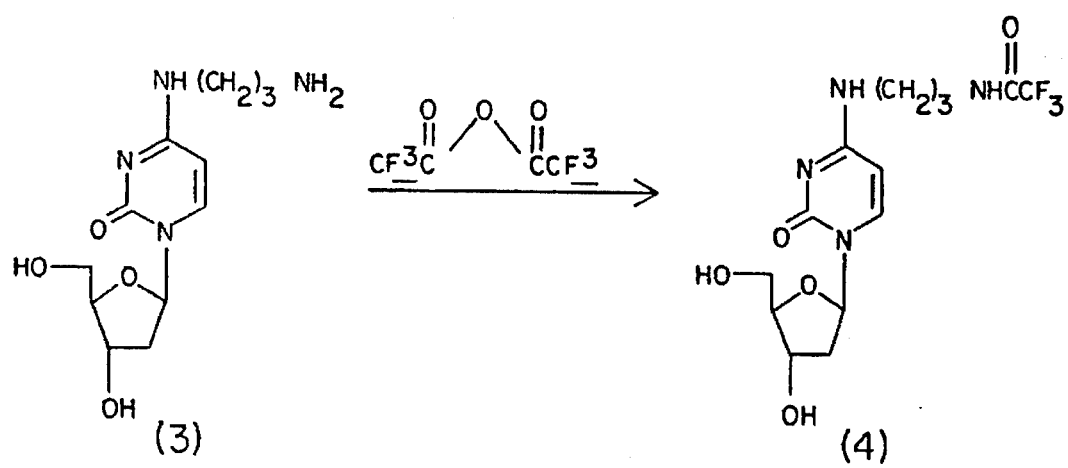
Figure 2:
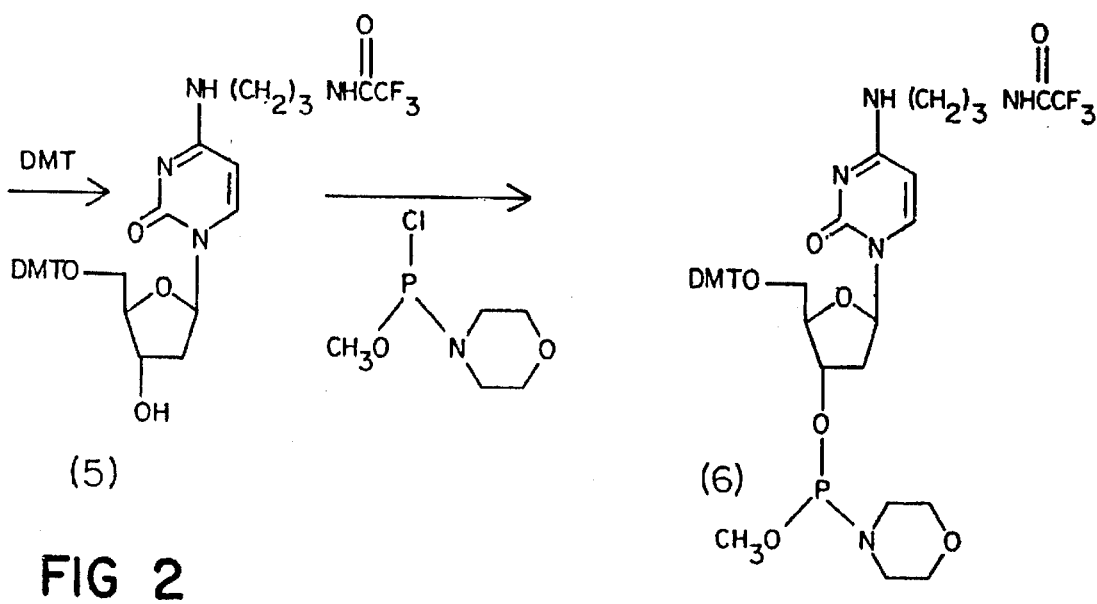

FIGS. 2–5 show the synthetic steps in the construction of the labeled oligonucleotide of FIG. 1. Referring to FIG. 2, the addition of the linker $(CH_2)_3$ and reactive group $NH_2$ is accomplished in a single step. This is followed by the addition to the NH, of the protective group $COCF_3$. The next step is protection of the C5 hydroxyl with the protective group DMT. The remaining hydroxyl (C3) is then reacted with a phosphite reagent to provide a site for the attachment of the cytidine analog to the oligonucleotide.

Figure 3:
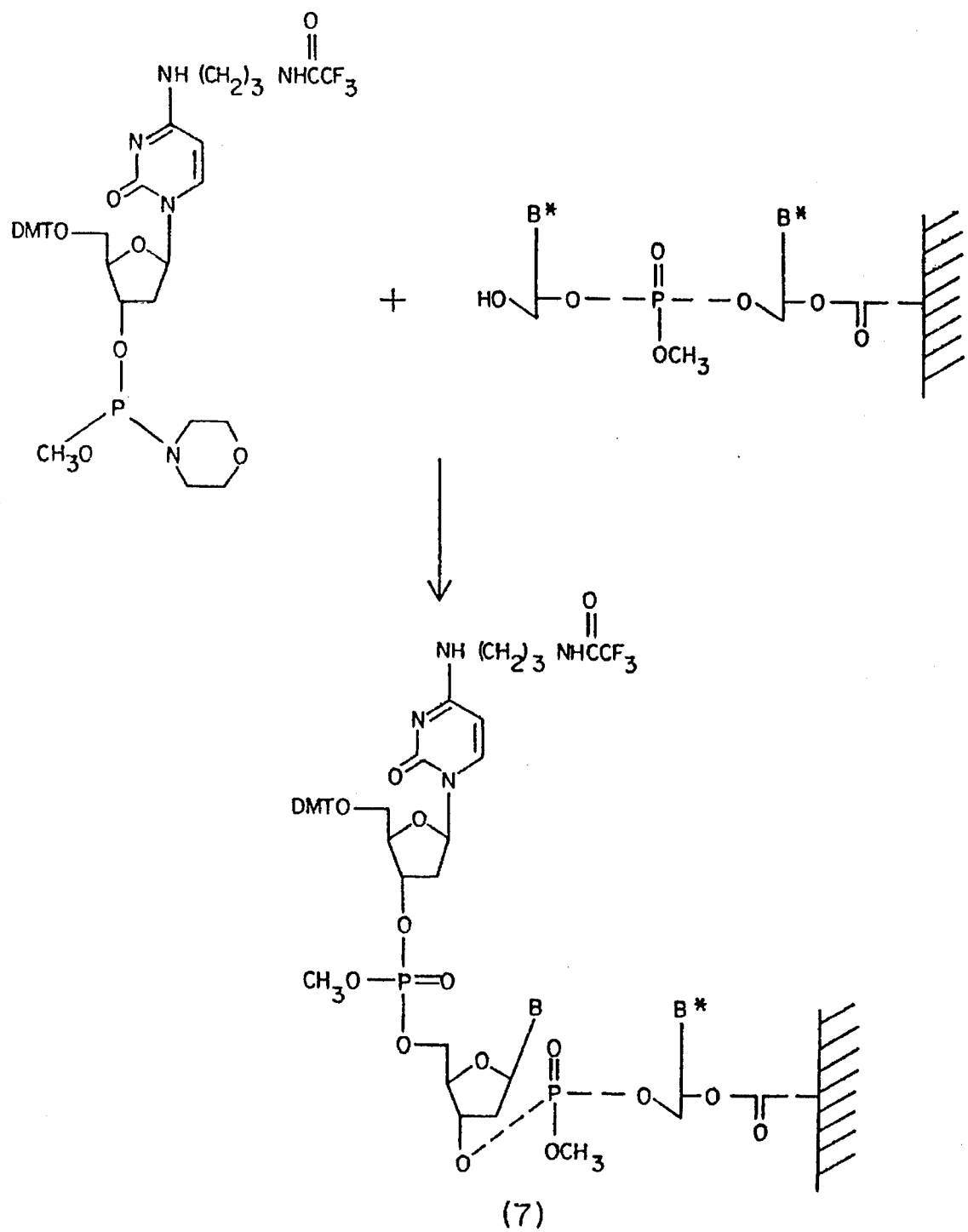
Figure 4:
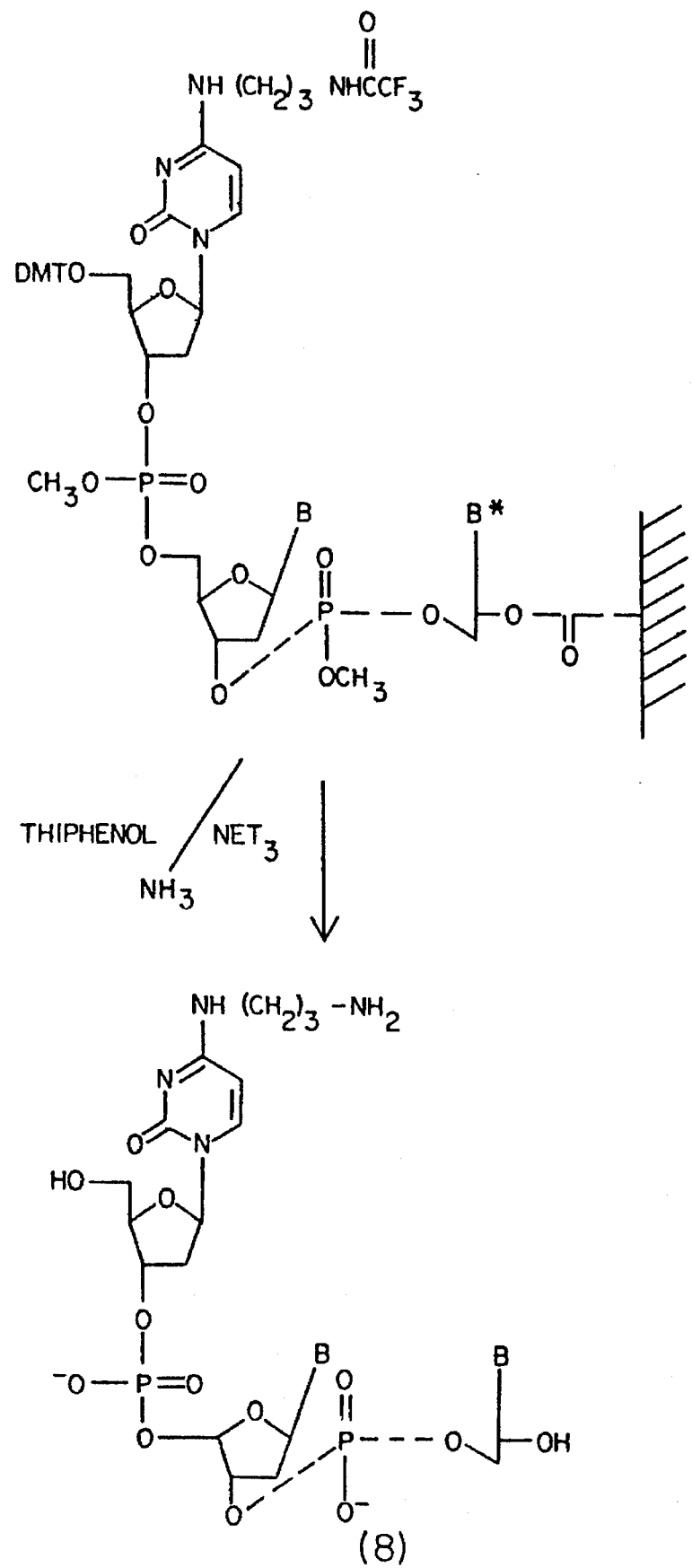
Figure 5:
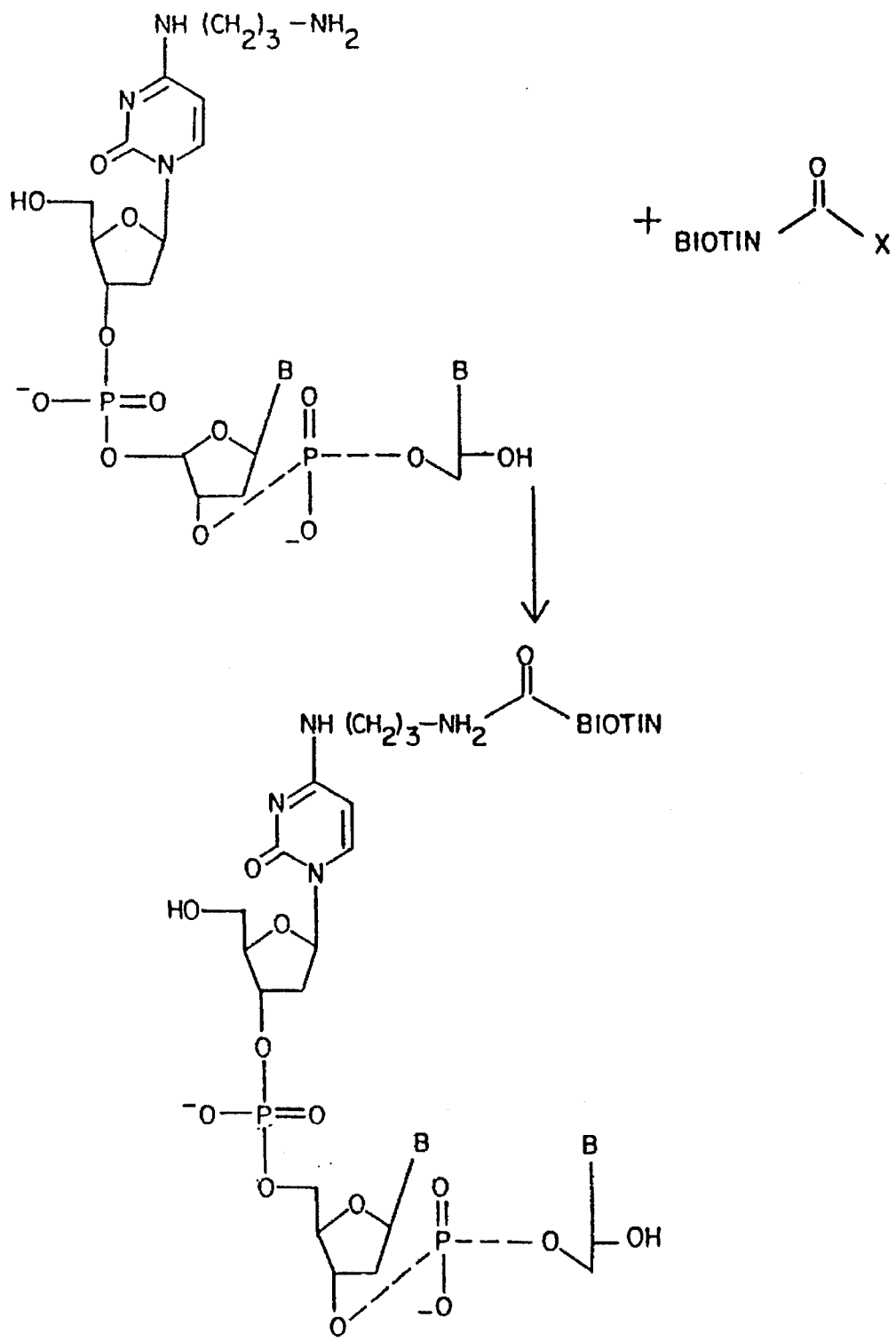

Referring to FIG. 3, the cytidine analog is then reacted with the oligonucleotide. Referring to FIG. 4, the protective groups $COCF_3$ and DMT are then removed and (FIG. 5) biotin added at the reactive $NH_2$ via an acylation reaction.

In more detail, the illustrated synthesis was carried out according to the following steps.

$N^4$-(3-aminopropyl)-2'-deoxycytidine (compound (3) of FIG. 2) has first prepared, as follows. A solution of sodium bisulfite (2M) and 1,3-diaminopropane (1M) was prepared by the addition of 1,3-diaminopropane (18.38 g, 0.25M, 20.8 ml) to an ice cold solution of sodium bisulfite (52.3 g, 0.5M) in distilled water (200 ml), the pH adjusted to 7 with concentrated HCl, and the volume made up to 250 ml with distilled water. 2'-deoxycytidine monohydrate (5.0 g, 20 mM) was added and the reaction mixture warmed to 70° C. and incubated overnight under argon. TLC in isopropanol: ammonia:water (60:15:5) gave two spots of equal intensity (Rf=0.29, 0.19). The reaction mixture was diluted 10-fold with 0.1MTRIS-HCl (30.28 g, 0.25 m, ph9) and the solution heated to 37° C. TLC as developed above gave one spot at Rf=0.29 after one hour. The solution was concentrated to approximately 150 ml and applied to a reversed phase C-18 column for desalting. The column was washed with two liters of distilled water and the product eluted with 10% acetonitrile in water to give compound (3) (2.0 g).

Next, compound (3) was suspended in a mixture of dichloromethane (50 ml)/triethylamine (4 ml) and cooled to 4° C. under argon. Trifluoroacetic anhydride (5.4 g, 25 mmol) was added dropwise by syringe over a ten minute period. The reaction mixture was stirred at room temperature for one hour and then an excess of trifluoroacetic anhydride (5.4 g, 25 mmol) was added. After one hour methanol (30 ml) was added and the solvent was then removed invacuo yielding a yellow oil (approximately 15 g), which was purified by column chromatography on silica gel (Baker Flash grade). Elution with dichloromethane:methanol (8:2) and evaporation of the solvent invacuo gave $^4$N-(3-trifluoroacetylaminopropyl)-2'-deoxycytidine (compound (4) of FIG. 2).

Compound (4) (1 g, 2.6 mmol) was co-evaporated with anhydrous pyridine (3×25 ml) and dissolved in anhydrous pyridine (30 ml). 4,4'-dimethoxytritylchloride (0.97 g, 2.8 mmol) was added and the mixture stirred at room temperature for one hour. Methanol (30 ml) was added and then the reaction mixture was concentrated invacuo. The residue was partitioned between dichloromethane (100 ml) and cold saturated sodium bicarbonate solution (100 ml). The aqueous layer was further extracted with dichloromethane (100 ml). The organic extracts were combined and dried using $Na_2SO_4$. Evaporation of the solvent invacuo gave a yellow oil which was purified by column chromatography on silica gel (Baker Flash Grade). Elution with dichloromethane/methanol/pyridine (950:49:1) and evaporation of the solvent invacuo gave 5'-O-(4,4-dimethoxytrityl)-$^4$N-(3-trifluoroacetylaminopropyl)-2'-deoxycytidine (compound (5) of FIG. 2).

Compound (5) (1.3 g, 1.9 mmol) was dissolved in a mixture of chloroform (10 ml, filtered through basic alumina) and diisopropylethylamine (1.3 ml, 7.6 mmol) under argon. To the ice cooled reaction mixture was added chloro-morpholino-methoxy-phosphine (0.29 ml, 2.85 mmol), dropwise, by syringe over three minutes. After 15 minutes at room temperature, the solution was transferred with 50 ml ethylacetate into a 250 ml separating funnel and extracted with cold, saturated sodium chloride solution (8×80 ml). The organic layer was dried ($Na_2SO_4$) and then concentrated invacuo to yield a buff colored foam. The foam was dissolved in toluene (15 ml) and added dropwise to hexane (200 ml) at −80° C. The colorless precipitate, collected at room temperature and dried under a stream of argon, was 5=-O-(4,4-dimethoxytrityl)-3'-methoxymorpholinophosphine-$^4$N-(3-trifluoroacetylaminopropyl)-2'-deoxycytidine (compound (6) of FIG. 2).

The next step was the incorporation of compound (6) into synthetic DNA. Compound (6), dissolved in acetonitrile (80 mg ml$^-$, 9.7 umolsml$^{-1}$) was used to functionalize oligonucleotides synthesised on an Applied Biosystems 380A DNA synthesiser, according to standard techniques. This resulted in functionalized oligonucleotide (7) of FIG. 3.

Following deprotection by treatment with thiophenol, ammonia and acetic acid to form the deprotected oligonucleotide (8) of FIG. 4, labeling with biotin was carried out as follows.

To oligonucleotide (8) (25 ug, 2.5×10$^{-9}$ moles) dissolved in 0.1M sodium borate, pH 8.0, was added the N-hydroxysuccinimide ester of biotin amino caproic acid (23 µg, 5×10$^{-8}$ moles) (Enzo Biochem) in dimethyl formamide (3 µl), and the reaction allowed to proceed for 4 hours. Residual biotin acylating reagent was removed from the biotinylated oligomer by chromatography on Sephadex G50. Further purification can be accomplished by reverse phase high performance liquid chromatography.

Use

The oligonucleotides which have been labeled using the cytidine analogs of the invention are used in nucleic acid hybridization reactions to detect nucleic acid sequences characteristic of specific bacteria, viruses, or cells, according to conventional techniques, e.g., as described in Landes U.S. Pat. Appln. Ser. No. 529,044, filed Sep. 2, 1983, now U.S. Pat. No. 4,624,501 assigned to the same assignee as the present application, hereby incorporated by reference.

We claim:

1. A modified cytidine having the formula

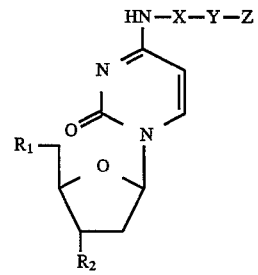

in which

X is a linker containing between 1 and 18 carbon atoms inclusive;

Y is —NH—;

Z is N-formyl, N-acetyl, N-o-nitrophenylacetyl, N-o-nitrophenoxyacetyl, N-acetoacetyl, N-3-phenylpropionyl, N-3(p-hydroxyphenyl)propionyl, N-2-methyl-2-(o-nitrophenoxy)propionyl, N-2-methyl-2-(o-phenylazophenoxy)propionyl, N-4-chlorobutyryl, N-o-nitrocinnamoyl, N-picolinoyl, N-(N'-acetylmethionyl), N-benzoyl, N-phthaloyl, N-dithiasuccinoyl; N-methoxy carbamyl, N-9-fluorenylmethoxy carbamyl, N-2,2,2-trichloroethoxy carbamyl, N-2-trimethylsilylethoxy carbamyl, N-1,1-dimethylpropynoxy carbamyl, N-1-methyl-1-phenylethoxy carbamyl, N-1-ethyl-1-(4-biphenylyl) ethoxy carbamyl, N-1-1-dimethyl-2-haloethoxy carbamyl, N-1-1-dimethyl-2-cyanoethoxy carbamyl, N-t-butoxy carbamyl, N-cyclobutoxy carbamyl, N-1-methylcyclobutoxy carbamyl, N-1-adamantyloxy carbamyl, N-vinyloxy carbamyl, N-allyloxy carbamyl, N-cinnamyloxy carbamyl, N-8-quinolyl carbamyl, N-hydroxypiperidinyloxy carbamyl, N-4,5-diphenyl-3-oxazolin-2-one, N-benzyloxy carbamyl, N-p-nitrobenzyloxy carbamyl, N-3,4-dimethoxy-6-nitrobenzyloxy carbamyl, N-2-4-dichlorobenzyloxy carbamyl, N-5-benzisoxazolylmethoxy carbamyl, N-9-anthrymethoxy carbamyl, N-diphenylmethoxy carbamyl, N-isonicotinyloxy carbamyl, N-S-benzylthio carbamyl, N-(N'-phenylaminothiocarbonyl); N-allyl, N-phenacyl, N-3-acetoxypropyl, N-methoxymethyl, N-benzyloxymethyl, N-pivaloyloxymethyl, N-tetrahydropyranyl, N-2,4-dinitrophenyl, N-benzyl, N-o-nitrobenzyl, N-di(p-methoxyphenyl)methyl, N-triphenylmethyl, N-(p-methoxyphenyl) diphenylmethyl, N-diphenyl-4-pyridylmethyl, N-2-picolyl, N-isopropylidene, N-benzylidene, N-p-nitrobenzylidene, N-salicylidene, N-(5,5-dimethyl-3-oxo-1-cyclohexenyl), N-NO$_2$ N-diphenylphosphinyl, N-dimethylthiophosphinyl, N-benzenesulfenyl, N-o-nitrobenzenesulfenyl, N-2,4,6-trimethylbenzenesulfonyl, N-toluenesulfonyl, N-benzylsulfonyl, N-trifluoromethylsulfonyl, and N-phenacylsulfonyl; and each $R_1$ and $R_2$ is —OH, —SH, or —H; provided that at least one of $R_1$ and $R_2$ must be —OH or —SH.

2. The modified cytidine of claim 1, wherein X is —(CH$_2$)$_n$ with n being an integer between 2 and 6, inclusive.

3. The modified cytidine of claim 2, wherein n is 3.

4. The modified cytidine of claim 3, wherein each $R_1$ and $R_2$ is —OH.

5. An oligonucleotide containing at least one modified nucleotide with a base of the formula:

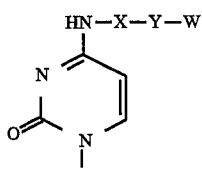

in which
X is a linker containing between 1 and 18 carbon atoms inclusive;
Y is —NH—; and
W is a detectable reporter group with the proviso that the reporter group is not fluorescein.

6. The oligonucleotide of claim 5, wherein X is —(CH$_2$)$_n$ with n being an integer between 2 and 6, inclusive.

7. The oligonucleotide of claim 5, wherein said detectable reporter group is biotin or a fluorophore.

8. The oligonucleotide of claim 6, wherein said detectable reporter group is biotin or a fluorophore.

9. The oligonucleotide of claim 5, wherein said modified nucleotide is at one end of said oligonucleotide.

10. The oligonucleotide of claim 6, wherein said modified nucleotide is at one end of said oligonucleotide.

11. The oligonucleotide of claim 7, wherein said modified nucleotide is at one end of said oligonucleotide.

12. The oligonucleotide of claim 8, wherein said modified nucleotide is at one end of said oligonucleotide.

13. A process for synthesizing an oligonucleotide which includes the repeated steps of joining a predetermined number of nucleoside via a phosphate bridge between their sugar moieties, wherein the improvement comprises using a modified nucleoside in at least one of the joining steps, said modified nucleoside having the formula

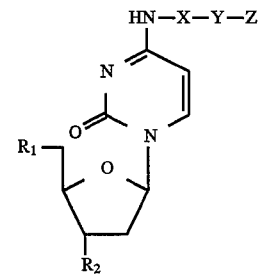

in which
X is a linker containing between 1 and 18 carbon atoms inclusive;
Y is —NH— or N=;
Z is N-formyl, N-acetyl, N-trichloroacetyl, N-trifluoroacetyl, N-o-nitrophenylacetyl, N-o-nitrophenoxyacetyl, N-acetoacetyl, N-3-phenylpropionyl, N-3(p-hydroxyphenyl)propionyl, N-2-methyl-2-(o-nitrophenoxy)propionyl, N-2-methyl-2-o-phenylazophenoxy)propionyl, N-4-chlorobutyryl, N-o-nitrocinnamoyl, N-picolinoyl, N-(N'-acetylmethionyl), N-benzoyl, N-phthaloyl, N-dithiasuccinoyl; N-methoxy carbamyl, N-9-fluorenylmethoxy carbamyl, N-2,2,2-trichloroethoxy carbamyl, N-2-trimethylsilylethoxy carbamyl, N-1,1-dimethylpropynoxy carbamyl, N-1-methyl-1-phenylethoxy carbamyl, N-1-ethyl-1-(4-biphenylyl) ethoxy carbamyl, N-1-1-dimethyl-2-haloethoxy carbamyl, N-1-1-dimethyl-2-cyanoethoxy carbamyl, N-t-butoxy carbamyl, cyclobutoxy carbamyl, N-1-methylcyclobutoxy carbamyl, N-1-adamantyloxy carbamyl, N-vinyloxy carbamyl, N-allyloxy carbamyl, N-cinnamyloxy carbamyl, N-8-quinolyloxy carbamyl, N-hydroxypiperidinyloxy carbamyl, N-4,5-diphenyl-3-oxazolin-2-one, N-benzyloxy carbamyl, N-p-nitrobenzyloxy carbamyl, N-3,4-dimethoxy-6-nitrobenzyloxy carbamyl, N-2-4-dichlorobenzyloxy carbamyl, N-5-benzisoxazolylmethoxy carbamyl, N-9-anthrymethoxy carbamyl, N-diphenylmethoxy carbamyl, N-isonicotinyloxy carbamyl, N-S-benzylthio carbamyl, N-(N'-phenylaminothiocarbonyl); N-allyl, N-phenacyl, N-3-acetoxypropyl, N-methoxymethyl, N-benzyloxymethyl, N-pivaloyloxymethyl, N-tetrahydropyranyl, N-2,4-dinitrophenyl, N-benzyl, N-o-nitrobenzyl, N-di(p-methoxyphenyl)methyl, N-triphenylmethyl, N-(p-methoxyphenyl) diphenylmethyl, N-diphenyl-4-pyridylmethyl, N-2-picolyl, N-isopropylidene, N-benzylidene, N-p-nitrobenzylidene, N-salicylidene, N-(5,5-dimethyl-3-oxo-1-cyclohexenyl), N-NO$_2$, N-diphenylphosphinyl, N-dimethylthiophosphinyl, N-benzenesulfenyl, N-o-nitrobenzenesulfenyl, N-2,4,6-trimethylbenzenesulfonyl, N-toluenesulfonyl, N-benzylsulfonyl, N-trifluoromethylsulfonyl, and N-phenacylsulfonyl; and each $R_1$ and $R_2$ is —OH, —SH, or —H; provided that at least one of $R_1$ and $R_2$ must be —OH or —SH.

14. The process of claim 13 wherein the improvement further comprising removing Z from said modified nucleoside after all of said predetermined number of nucleosides have been joined together and subsequently attaching a detectable reporter group to Y to replace Z of said modified nucleoside.

15. The process of claim 13, wherein X is —$(CH_2)_n$ with n being an integer between 2 and 6, inclusive.

16. The process of claim 15, wherein Z is

17. The process of claim 15, wherein each $R_1$ and $R_2$ is —OH.

18. The process of claim 17, wherein said modified nucleoside is used in the last joining step.

19. The process of claim 14, wherein X is —$(CH_2)_n$ with n being an integer between 2 and 6, inclusive.

20. The process of claim 19, wherein Z is

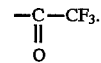

21. The process of claim 19, wherein each $R_1$ and $R_2$ is —OH.

22. The process of claim 21, wherein said detectable reporter group is biotin or a fluorophore.

23. The process of claim 22, wherein said modified nucleoside is used in the last joining step.

* * * * *